(12) United States Patent
Butler et al.

(10) Patent No.: US 8,968,369 B2
(45) Date of Patent: Mar. 3, 2015

(54) SPINE PLATE WITH BONE SCREW RELIEF AREA

(75) Inventors: Michael S. Butler, St. Charles, IL (US); Michael J. Milella, Jr., Schaumburg, IL (US)

(73) Assignee: Life Spine, Inc., Huntley, IL (US)

( * ) Notice: Subject to any disclaimer, the term of this patent is extended or adjusted under 35 U.S.C. 154(b) by 1347 days.

(21) Appl. No.: 12/072,357

(22) Filed: Feb. 26, 2008

(65) Prior Publication Data

US 2008/0208262 A1   Aug. 28, 2008

Related U.S. Application Data

(60) Provisional application No. 60/903,499, filed on Feb. 26, 2007.

(51) Int. Cl.
*A61B 17/80* (2006.01)
*A61B 17/70* (2006.01)
*A61B 17/86* (2006.01)

(52) U.S. Cl.
CPC ......... *A61B 17/8052* (2013.01); *A61B 17/7059* (2013.01); *A61B 17/8605* (2013.01)
USPC ............ 606/280; 606/286; 606/289; 606/291

(58) Field of Classification Search
CPC ...................................................... A61B 17/80
USPC .................................. 606/280, 286, 289, 291
See application file for complete search history.

(56) References Cited

U.S. PATENT DOCUMENTS

| | | | |
|---|---|---|---|
| 6,605,090 B1 * | 8/2003 | Trieu et al. | 606/281 |
| 2002/0077630 A1 | 6/2002 | Lin | |
| 2004/0097935 A1 | 5/2004 | Richelsoph et al. | |
| 2004/0127896 A1 * | 7/2004 | Lombardo et al. | 606/61 |
| 2005/0004574 A1 | 1/2005 | Muckter | |
| 2005/0137597 A1 | 6/2005 | Butler et al. | |
| 2005/0149026 A1 | 7/2005 | Butler et al. | |
| 2005/0277937 A1 | 12/2005 | Leung et al. | |
| 2006/0229618 A1 * | 10/2006 | Dube | 606/69 |
| 2006/0276793 A1 | 12/2006 | Berry | |
| 2008/0147125 A1 * | 6/2008 | Colleran et al. | 606/280 |

* cited by examiner

*Primary Examiner* — Nicholas Woodall
*Assistant Examiner* — Christine Nelson
(74) *Attorney, Agent, or Firm* — Foley & Lardner LLP

(57) ABSTRACT

A spine plate defines a body having a posterior surface or side and an anterior surface or side. The body also has a pair of bone screw bores for each vertebra to which the spine plate will be attached. The bone screw bores extend between the posterior side and the anterior side. A relief area is provided between each pair of bone screw bores in the anterior surface of the body. The relief area opens to both bone screw bores to allow displacement of the bone screw when entering the respective bone screw bore. The relief area also opens to both bone screw bores to permit an instrument to be received therein to remove a bone screw from one of the bone screw bores.

24 Claims, 15 Drawing Sheets

SPINE PLATE WITH BONE SCREW RELIEF AREA

RELATED APPLICATIONS

This patent application claims the benefit of and/or priority to U.S. Provisional Patent Application No. 60/903,499 filed Feb. 26, 2007, entitled "Spine Plates, Bone Screws and Spine Plate Constructs" the entire contents of which is specifically incorporated by reference.

BACKGROUND OF THE INVENTION

1. Field of the Invention

The present invention relates generally to devices for the internal fixation of the spine particularly within the fields of orthopedics and/or neurosurgery such as spinal implants for holding vertebral bones fixed relative to one another and, more particularly, to static bone fixation implants for use in spinal surgical procedures for stabilizing the relative motion of, temporarily or permanently immobilizing, bones of the spine.

2. Background Information

Spine plates have been used for more than 20 years to increase spine stability following single and multi-level spine surgery. Plates implanted during surgery for reasons such as disease, trauma, defect, accident or the like, are used to stabilize one or more spinal vertebrae. Stabilization leads to a proper healing or a desired outcome. The plate is mounted to one or more vertebrae during the surgery. Typically, bone screws are used to mount the plate to the one or more vertebrae. It is important during the mounting process that the plate be properly aligned on the vertebrae for receipt of the mounting screws.

In some instances, it is desirous to cause the fusion of two adjacent vertebrae. If this is the case, the surgeon makes an incision to reach the spine. Tissues and muscles are retracted (spread apart) to reveal the proper level in the spine. The cartilaginous material or disc between the two vertebrae is removed and the bone surface abraded to encourage a bleeding surface. Blood from the bleeding surfaces is desired in order for the bones to fuse. The space between the adjacent vertebrae is filled with bone graft. A plate is then screwed into the superior (top) and inferior (bottom) vertebrae. This stabilizes the spine to facilitate fusion and healing.

In all cases, the spine plates must be fastened to the vertebrae. This is accomplished by bone screws. The bone screws are received in bores of the spine plate and hold the spine plate to the vertebra. In order to prevent anti-rotation or "backing out" of the bone screw once it has been rotated into the bone (vertebra), caps or prong structures are placed into drive sockets in the heads of the bone screws. This detrimentally adds an extra component to the plate assembly or construct. It would be desirable to provide a spine plate and/or spine plate assembly that eliminates this extra component.

Moreover, bone screw bores of current spine plates do not have the configuration or geometry to allow angulation of bone screws as appropriate or to prohibit angulation of bone screws as appropriate while providing a positive retention of the bone screw by the plate alone. It would be desirable to provide a spine plate and/or spine plate assembly having bone screw bores that are configured to provide for angulation of a bone screw and/or the prohibition of angulation of a bone screw as appropriate while providing a positive retention of the bone screw by the plate alone.

Other objects will become apparent from the following.

SUMMARY OF THE INVENTION

A single to multi-level spine plate having a pair of bone screw bores for each vertebra includes a relief area that is provided between the bone screw bores of each pair of bone screw bores. The relief area opens to both bone screw bores of the bone screw bore pair to allow displacement of a bone screw when entering the respective bone screw bore. The relief area also permits an instrument to be received therein to remove a bone screw from one of the bone screw bores if necessary.

In one form, the spine plate defines a body having a posterior surface or side and an anterior surface or side. The body also has a pair of bone screw bores for each vertebra to which the spine plate will be attached. The bone screw bores extend between the posterior side and the anterior side. A relief area, channel or groove is provided between each pair of bone screw bores in the anterior surface of the body. The relief area opens to both bone screw bores to allow displacement of the bone screw when entering the respective bone screw bore. The relief area also opens to both bone screw bores to permit an instrument to be received therein to remove a bone screw from one of the bone screw bores.

The relief area preferably, but not necessarily, narrows between the pair of bone screw bores. In one form, the relief area is formed in an hour-glass shape.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Like reference numerals indicate the same or similar parts throughout the several figures.

Figure 1:
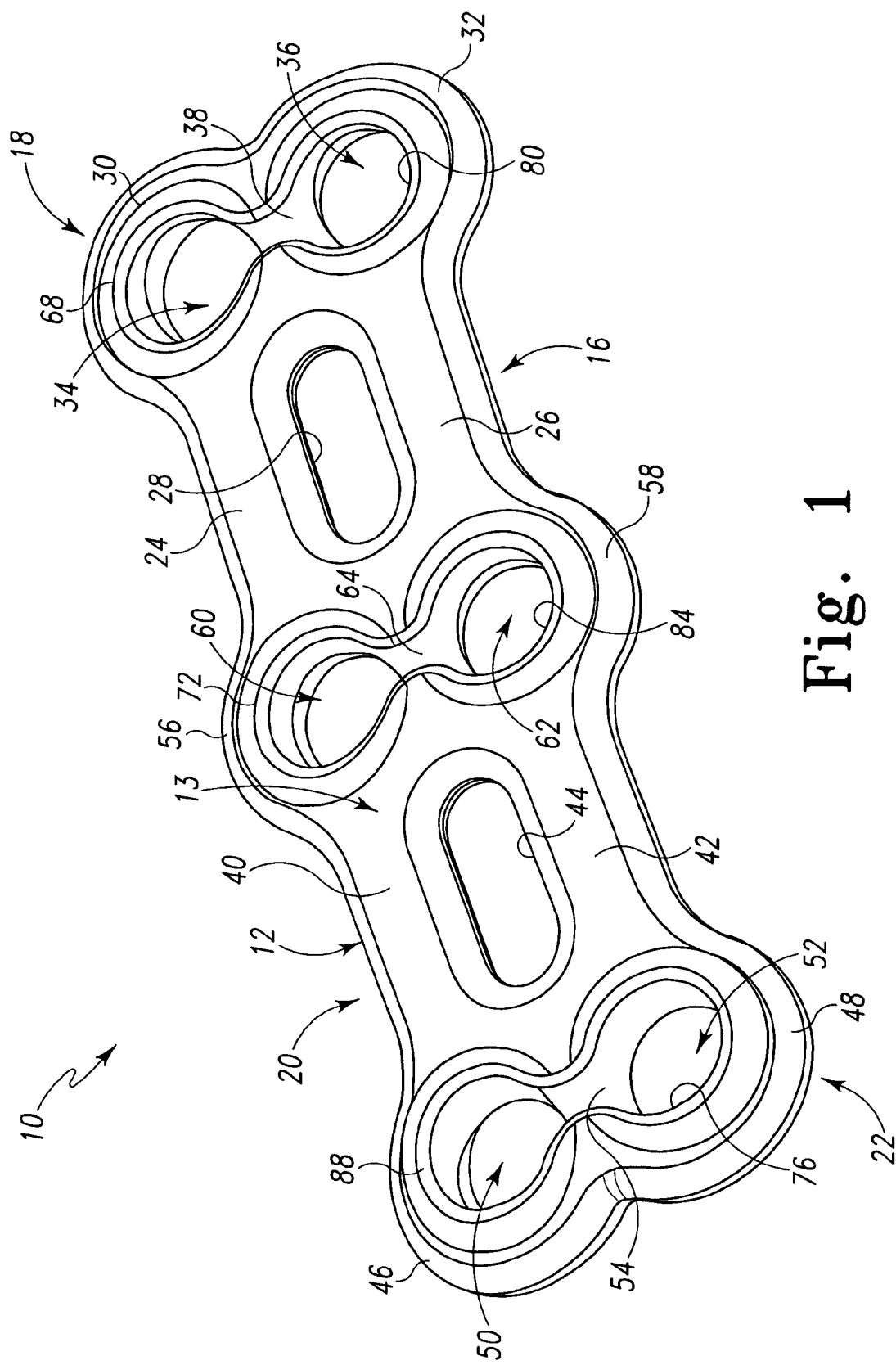
FIG. 1 is an anterior perspective view of an exemplary embodiment of a two level (2-L) spine plate fashioned in accordance with the present principles.
Figure 2:
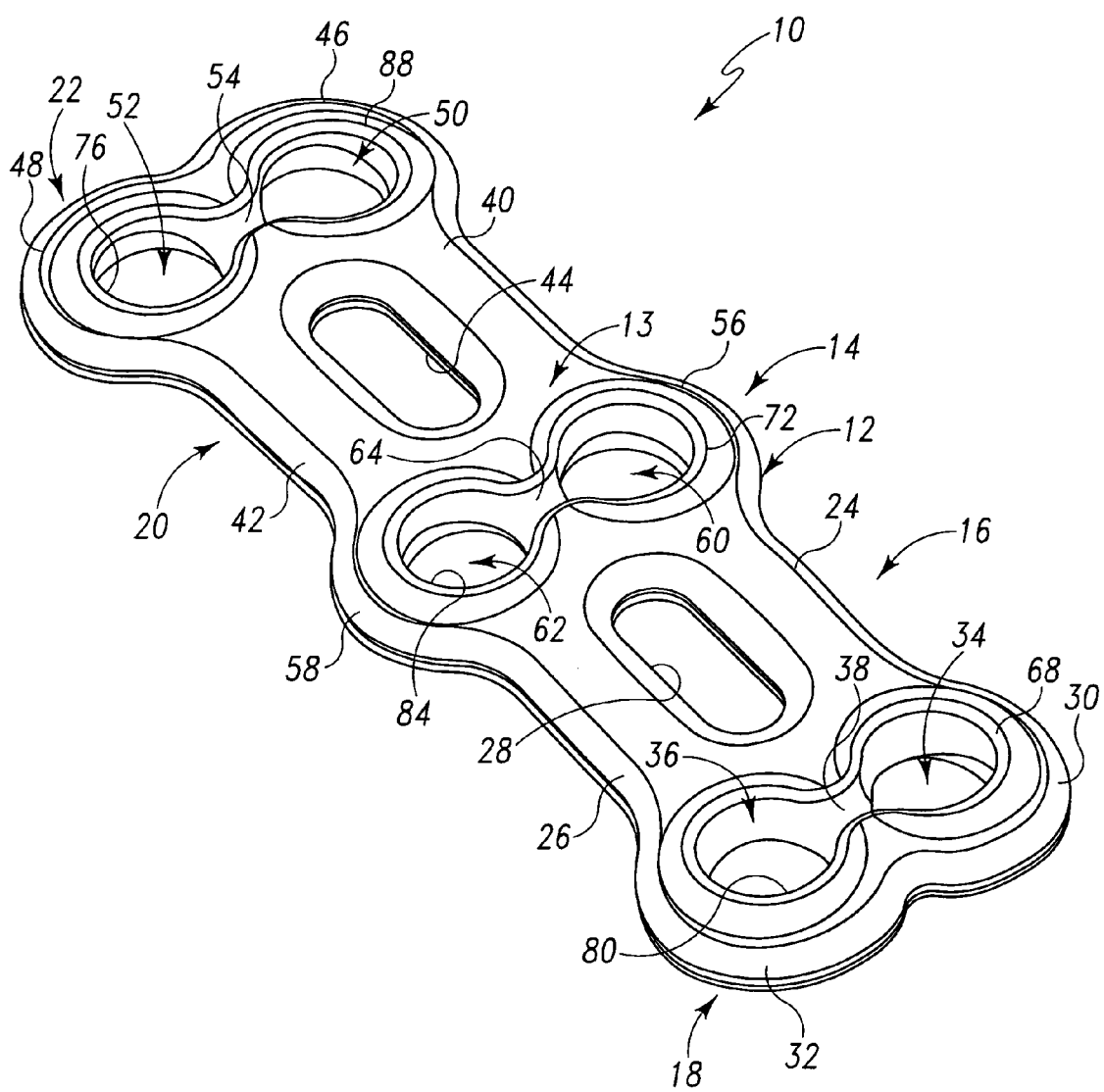
FIG. 2 is another anterior perspective view of the 2-L spine plate of FIG. 1.
Figure 3:
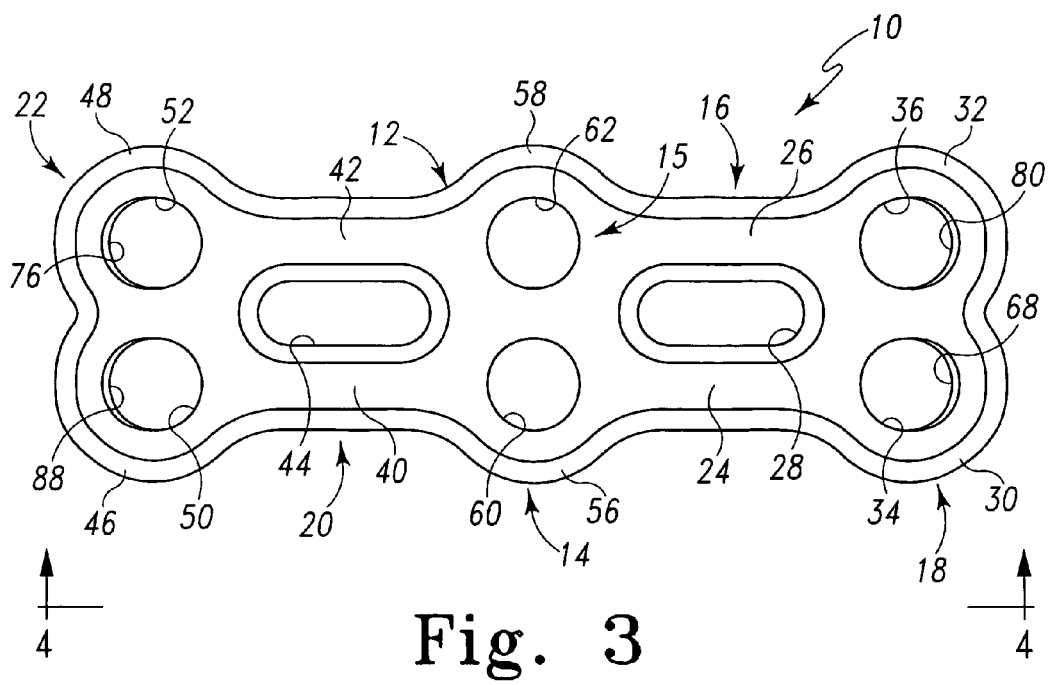
FIG. 3 is a posterior plan view of the 2-L spine plate of FIG. 1.
Figure 4:
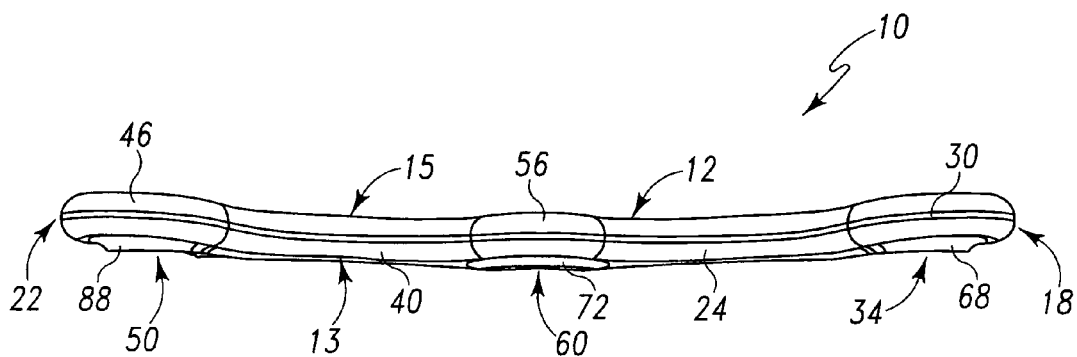
FIG. 4 is a side view of the 2-L spine plate of FIG. 3 taken along line 4-4 thereof.
Figure 6:
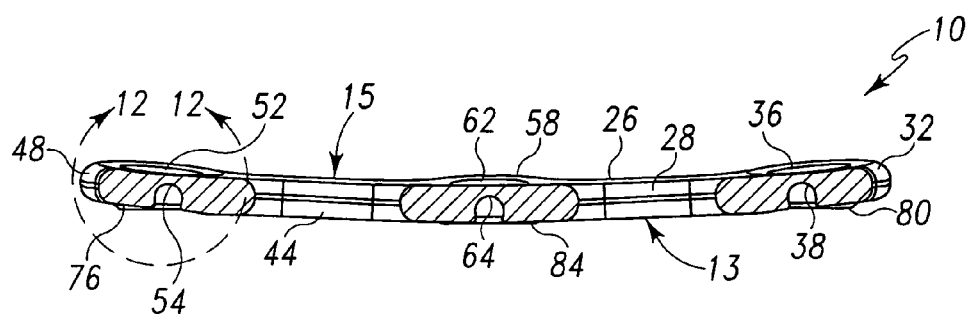
FIG. 6 is a sectional view of the 2-L spine plate of FIG. 5 taken along line 6-6 thereof.
Figure 5:
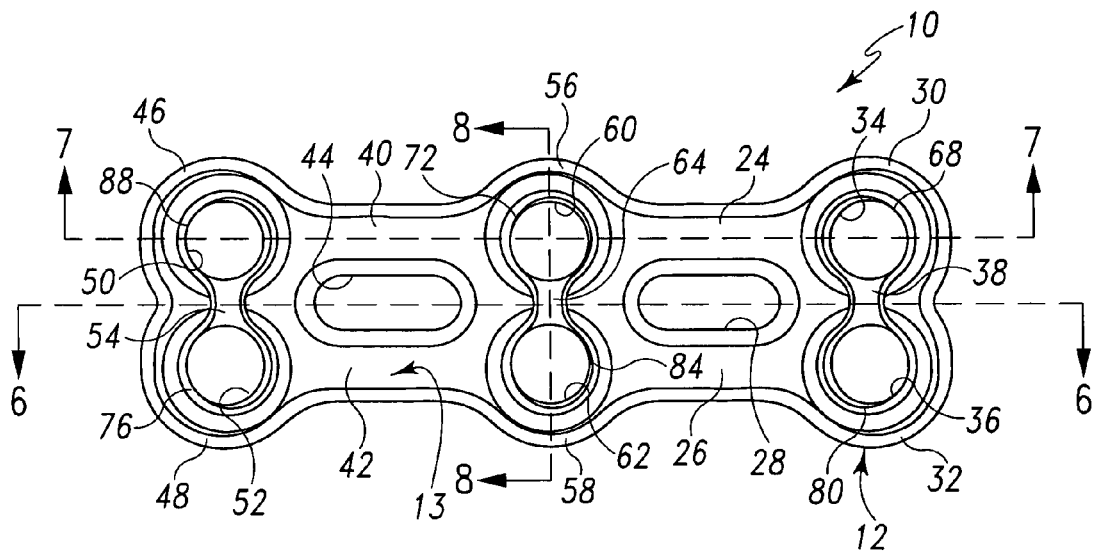
FIG. 5 is an anterior plan view of the 2-L spine plate of FIG. 1.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE PREFERRED EMBODIMENTS

Referring to the figures and particularly to FIGS. 1-12, there is depicted an embodiment of a two-level (2-L) spine or spinal plate generally designated 10 fashioned in accordance with the present principles. Single level and multiple level (up to five levels) spine plates are also contemplated that utilize the present principles. It should be understood that the 2-L spine plate 10 is representative of all such plates. These plates are adapted and/or configured to be placed onto vertebrae of the spine. The 2-L spine plate 10 is formed of a suitable biocompatible material such as titanium, stainless steel, alloys thereof, and other biomaterials.

The 2-L spine plate 10 is defined by a body 12 having an anterior side 13 and a posterior side 15. The body 12 is formed of a middle section 14, a first neck 16 extending from one side of the middle section 14 and terminating in a first end 18 distal the middle section 14, and a second neck 20 extending from another side of the middle section 14 and terminating in a second end 22 distal the middle section 14. It should be appreciated that the terms first and second are arbitrary unless indicated otherwise. As best discerned in FIGS. 4 and 6-9, the plate body 12 is curved or arched from end 18 to end 22 (along a saggittal plane). The plate body 12 may be made in various sizes.

The first neck 16 has a first opening or window 28 formed between the middle section 14 and the first end 18 and is preferably oval as shown, but may be other shapes as desired. The first opening 28 forms a graft window of and for the plate 10 and defines first and second neck portions 24 and 26 of the first neck 16. The first neck portion 24 of the first neck 16 extends from one side of a first side boss 56 of the middle section 14 to a first end boss 30 of the first end 18. The second neck portion 26 of the first neck 16 extends from one side of a second side boss 58 of the middle section 14 to a second end boss 32 of the first end 18. The second neck 20 has a second opening or window 44 formed between the middle section 14 and the second end 22 and is preferably oval as shown, but may be other shapes as desired. The second opening 44 forms a graft window of and for the plate 10 and defines first and second neck portions 40 and 42 of the second neck 20. The first neck portion 40 of the second neck 20 extends from another side of the first side boss 56 of the middle section 14 to a first end boss 46 of the second end 22. The second neck portion 42 of the second neck 20 extends from another side of the second side boss 58 of the middle section 14 to a second end boss 48 of the second end 22.

Figure 7:
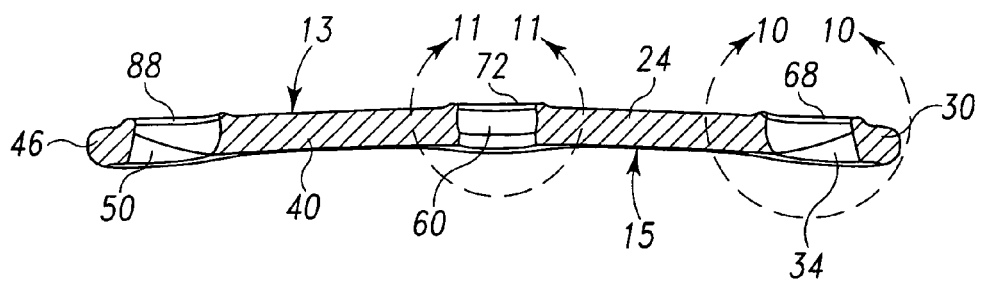
FIG. 7 is a sectional view of the 2-L spine plate of FIG. 5 taken along line 7-7 thereof.
Figure 8:
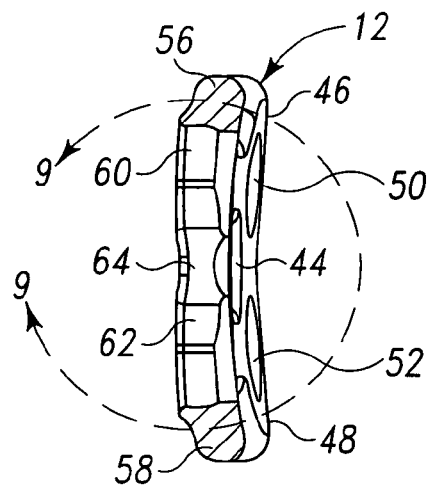
FIG. 8 is a sectional view of the 2-L spine plate of FIG. 5 taken along line 8-8 thereof.
Figure 9:
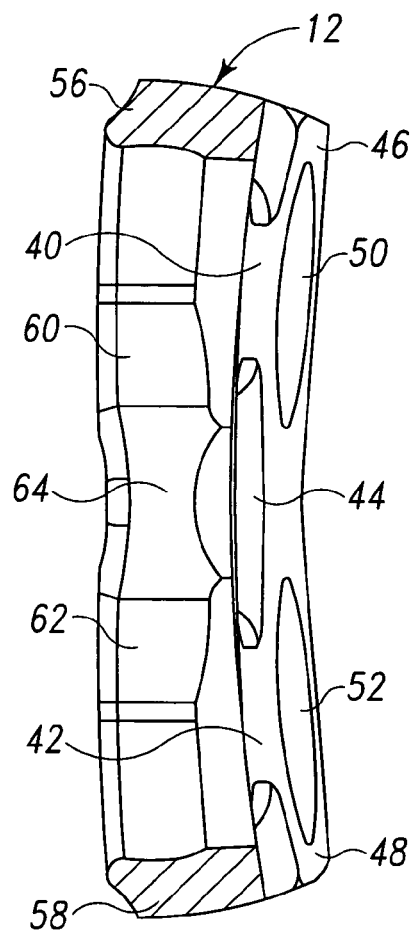
FIG. 9 is an enlarged portion of the sectional view of FIG. 8 taken along circle 9-9 thereof.
Figure 10:
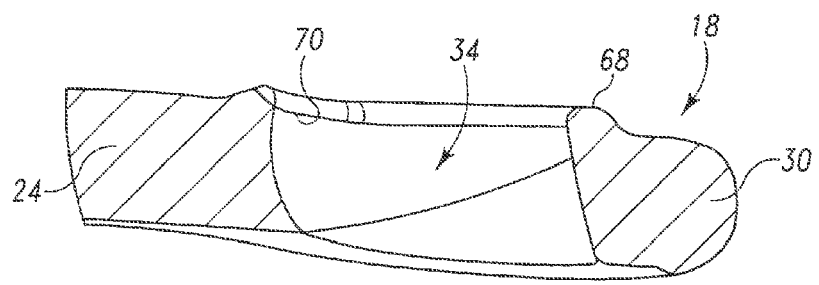
FIG. 10 is an enlarged portion of the sectional view of FIG. 7 taken along circle 10-10 thereof.
Figure 11:
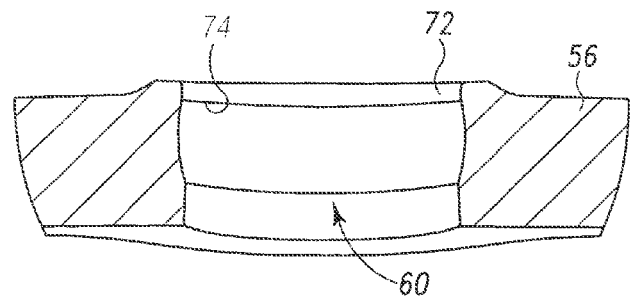
FIG. 11 Is an enlarged portion of the sectional view of FIG. 7 taken along circle 11-11 thereof.
Figure 25:
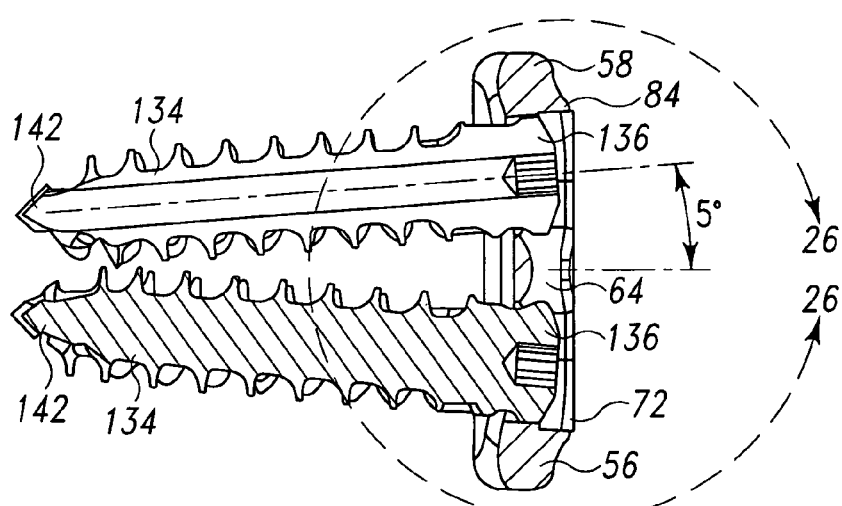
FIG. 25 is a sectional view of the present 2-L spine plate with various ones of the present bone screws of FIG. 24 taken along line 25-25 thereof.
Figure 26:
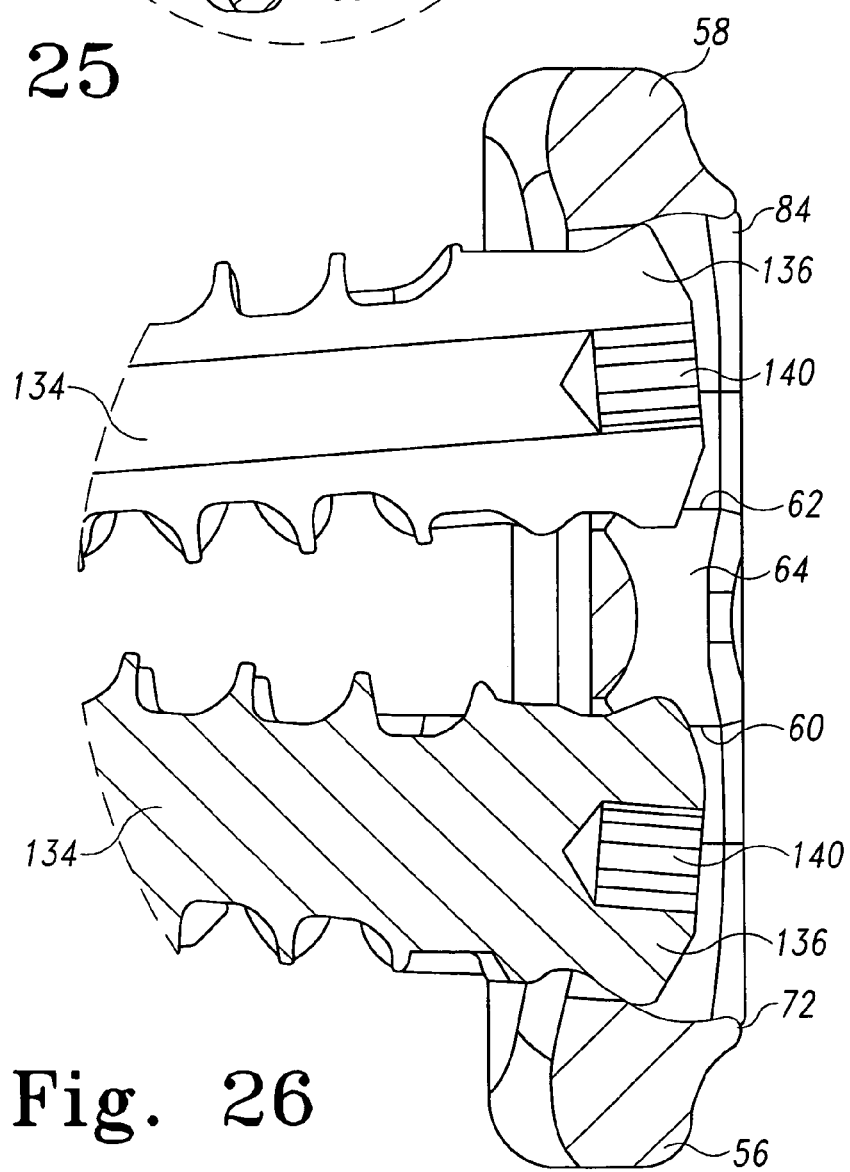
FIG. 26 is an enlarged portion of the sectional view of FIG. 25 taken along circle 26-26 thereof.

The middle section 14 has a first bone screw bore 60 formed in the side boss 56. The first bone screw bore 60 is configured to accommodate a bone screw such as described and/or shown herein. Moreover, as best seen in FIGS. 7 and 11, the first bone screw bore 60 is configured as a cylindrical hole having an arcuate lip 72 formed around a majority of the annular rim of the bore 60. The lip 72 forms an undercut 74 for the bone screw to "snap" into in order to retain the bone screw into the bore 60 when so implanted (see, e.g. FIG. 10). The bore 60 has sidewalls that are spherical and configured to provide a ten degree (10°) angulation range in the medial-lateral direction for a bone screw (see, e.g. FIGS. 25 and 26).

Figure 24:
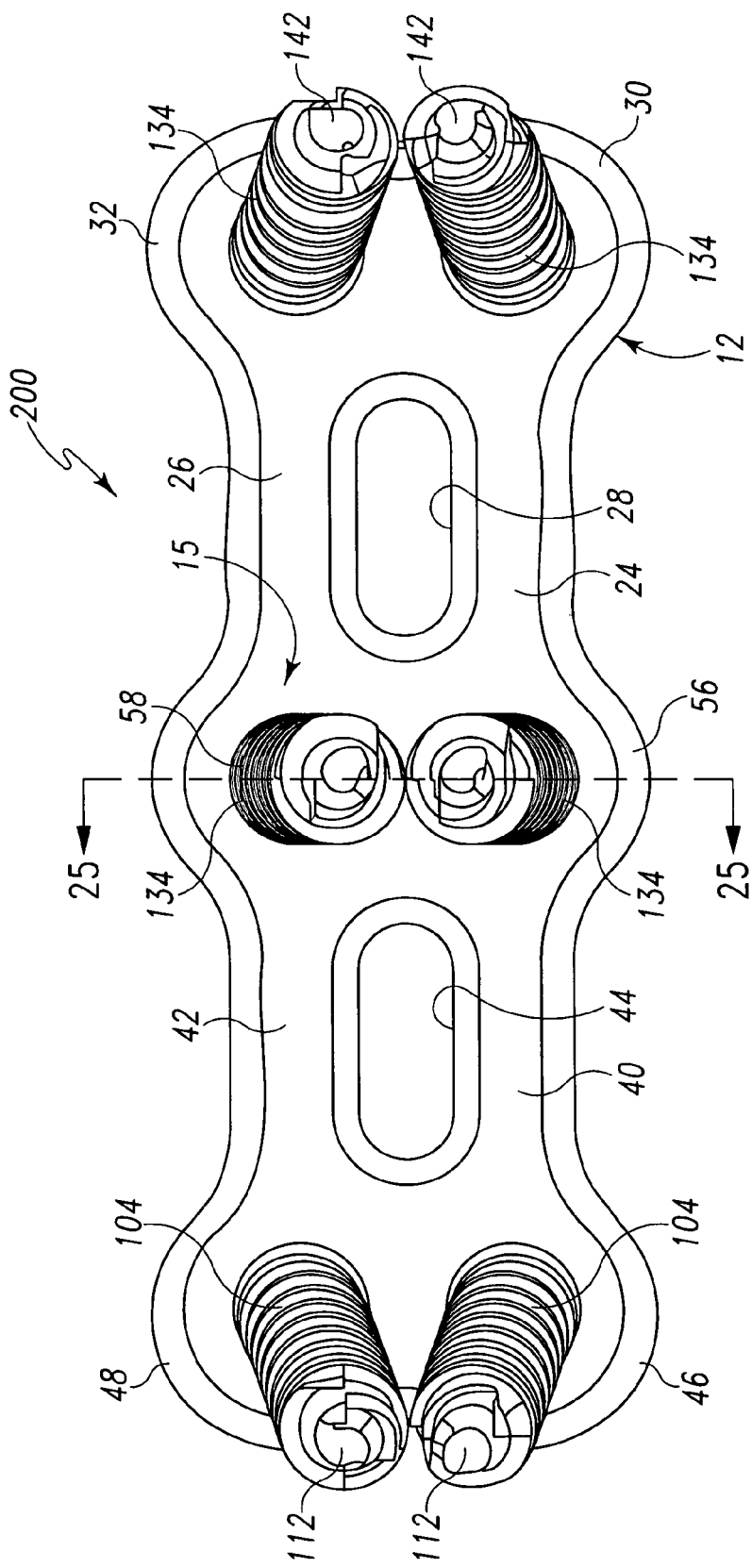
FIG. 24 is a posterior plan view of the present 2-L spine plate with various ones of the present bone screws of FIG. 22.

A second bone screw bore 62 is formed in the side boss 58 of the middle section 14. The second screw bore 62 is configured to accommodate a bone screw such as described and/or shown herein. The second bone screw bore 62 is configured as a cylindrical hole having an arcuate lip 84 formed around a majority of the annular rim of the bore 62. The lip 84 forms an undercut in like manner to undercut 74 of bore 60, for the bone screw to "snap" into in order to retain the bone screw into the bore 62 when so implanted. The bore 62 has sidewalls that are spherical and configured to provide a ten degree (10°) angulation range in the medial-lateral direction for a bone screw (see, e.g. FIGS. 25 and 26). As can be discerned in FIGS. 24, 25 and 26, the bone screw bore 60 provides angulation in a medial direction (inwards) from a longitudinal axis of the bone screw therein, while the bone screw bore 62 provides angulation in a medial direction (inwards) from a longitudinal axis of the bone screw therein.

A relief area, trough, channel or the like 64 is provided in the anterior side 13 of the plate body 12 between the first and second bores 60 and 62 of the middle section 14. The relief area 64 is preferably, but not necessarily, hour-glass shaped (see, e.g. FIG. 5) having ends that open into or provide communication with the respective first and second bores 60 and 62. As detailed in FIG. 12 with respect to the bone screw bore 52 wherein the relief area thereof is labeled 54, the relief area is configured to allow the bone screw to displace within the screw pockets when entering the bore. The relief area also is used to remove the bone screw by placing an instrument in the hole of the relief area and splaying open the screw holes.

Figure 22:
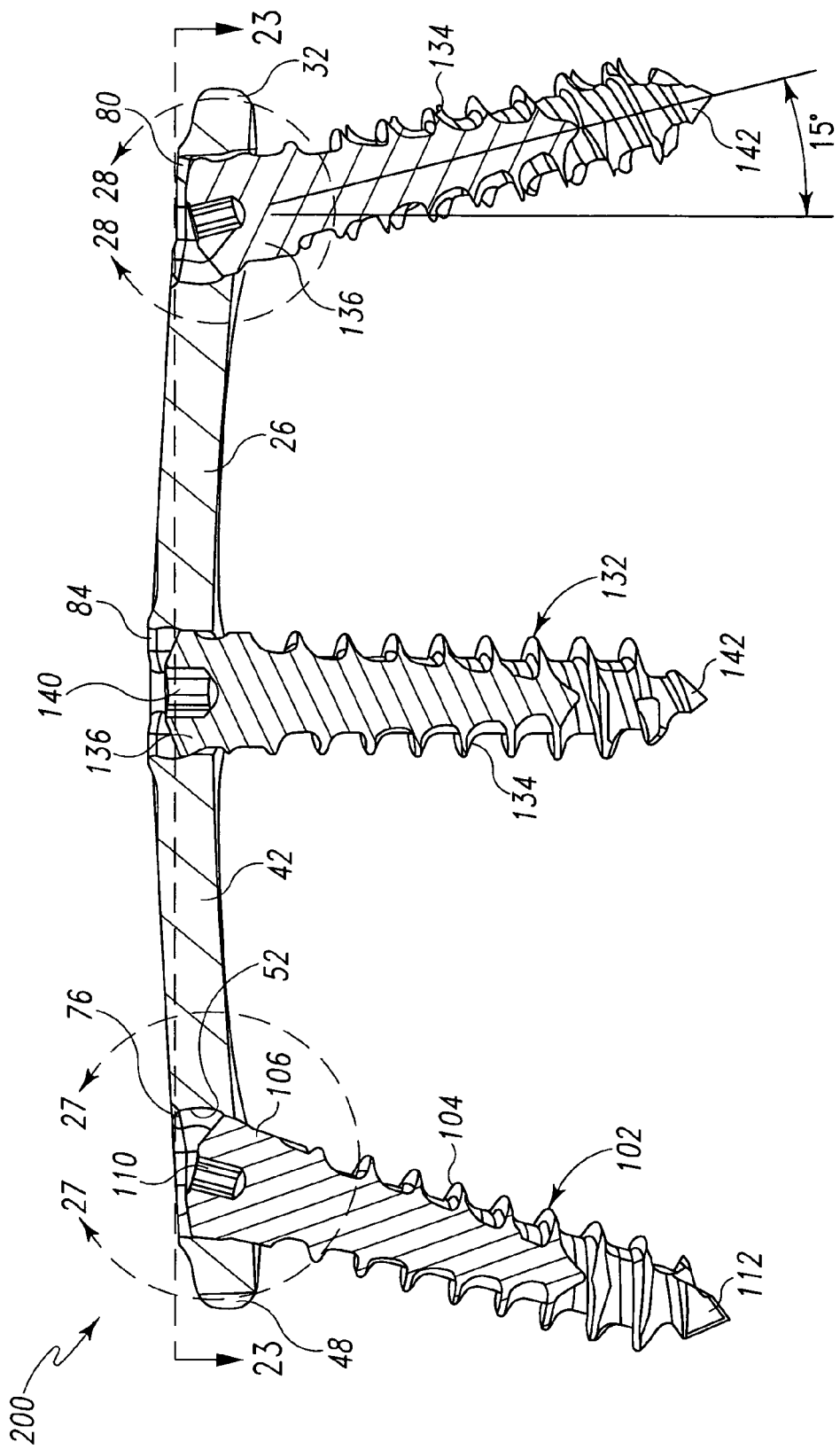
FIG. 22 is a sectional view of the 2-L spine plate with various ones of the present bone screws situated therein of FIG. 23 taken along line 22-22 thereof.

The first end 18 has a first bone screw bore 34 formed in the first boss 32. The first bone screw bore 34 is configured to accommodate a bone screw such as described and/or shown herein. Moreover, as best seen in FIGS. 7 and 10, the first bone screw bore 34 is configured as a cylindrical hole having an arcuate lip 68 formed around a majority of the annular rim of the bore 34. The lip 68 forms an undercut 70 for the bone screw to "snap" into in order to retain the bone screw into the bore 34 when so implanted. The bore 34 has sidewalls that are spherical and configured to provide bone screw angulation. The bore 34 is configured to provide a thirty degree (30°) angulation range in the cephalad-caudal direction for a bone screw (see, e.g. FIGS. 22 and 24).

The first end 18 also has a second bone screw bore 36 formed in the second boss 34. The second bone screw bore 36 is configured to accommodate a bone screw such as described and/or shown herein. The second first bone screw bore 36 is configured as a cylindrical hole having an arcuate lip 80 formed around a majority of the annular rim of the bore 36. The lip 80 forms an undercut, in like manner to undercut 70 of bore 34, for the bone screw to "snap" into in order to retain the bone screw into the bore 36 when so implanted. The bore 36 has sidewalls that are spherical and configured to provide bone screw angulation. The bore 34 is configured to provide a thirty degree (30°) angulation range in the cephalad-caudal direction for a bone screw (see, e.g. FIGS. 22 and 24). As can be discerned in FIGS. 24, 25 and 26, the bone screw bore 34 provides angulation in a medial direction (inwards) from a longitudinal axis of the bone screw therein, while the bone screw bore 36 provides angulation in a medial direction (inwards) from a longitudinal axis of the bone screw therein.

A relief area, trough, channel or the like 38 is provided in the anterior side 13 of the plate body 12 between the first and second bores 34 and 36 of the first end 18. The relief area 38 is preferably, but not necessarily, hour-glass shaped (see, e.g. FIG. 5) having ends that open into or provide communication with the respective first and second bores 34 and 36. As detailed in FIG. 12 with respect to the bone screw bore 52 wherein the relief area thereof is labeled 54, the relief area is configured to allow the bone screw to displace within the screw pockets when entering the bore. The relief area also is used to remove the bone screw by placing an instrument in the hole of the relief area and splaying open the screw holes.

The second end 22 of the body 12 of the spine plate 10 has a first bone screw bore 50 formed in the first boss 46 of the second end plate 22. The first bone screw bore 50 is configured to accommodate a bone screw such as described and/or shown herein. Moreover, the first bone screw bore 50 is configured as a cylindrical hole having an arcuate lip 88 formed around a majority of the annular rim of the bore 50. The lip 88 forms an undercut, in like manner to undercut 70 of bore 34, for the bone screw to "snap" into in order to retain the bone screw into the bore 50 when so implanted. Again, in like manner to the bore 34 but configured opposite thereto, the bore 50 has sidewalls that are spherical and configured to provide bone screw angulation. The bore 50 is configured to provide a thirty degree (30°) angulation range in the cephalad-caudal direction for a bone screw but opposite for those of the first end 18 (see, e.g. FIGS. 22 and 24).

The second end 22 of the body 12 of the spine plate 10 has a second bone screw bore 52 formed in the second boss 34 of the second end plate 22. The second bone screw bore 52 is configured to accommodate a bone screw such as described and/or shown herein. Moreover, the second first bone screw bore 52 is configured as a cylindrical hole having an arcuate lip 76 formed around a majority of the annular rim of the bore 52. The lip 76 forms an undercut 78 (see FIGS. 7 and 12) for the bone screw to "snap" into in order to retain the bone screw into the bore 52 when so implanted. The bore 52 has sidewalls that are spherical and configured to provide bone screw angulation. The bore 52 is configured to provide a thirty degree (30°) angulation range in the cephalad-caudal direction for a bone screw but opposite to that of the first end 18 (see, e.g. FIGS. 22 and 24).

Figure 12:
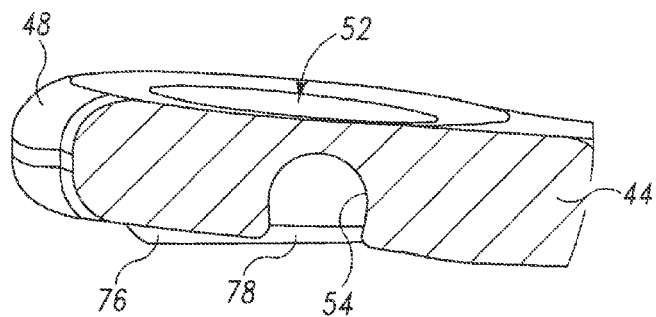
FIG. 12 is an enlarged portion of the sectional view of FIG. 6 taken along circle 12-12 thereof.

A relief area, trough, channel or the like 54 is provided in the anterior side 13 of the plate body 12 between the first and second bores 50 and 52 of the second end 22 (see, e.g. FIG. 12). The relief area 54 is preferably, but not necessarily, hour-glass shaped having ends that open into or provide communication with the respective first and second bores 50 and 52. As detailed in FIG. 12, the relief area is configured to allow the bone screw to displace within the screw pockets when entering the bore. The relief area also is used to remove the bone screw by placing an instrument in the hole of the relief area and splaying open the screw holes.

The bone screw bores or screw pockets (as defined by their geometry and/or configuration) may have a fixed or pre-disposed angulation rather than provide for a variable angulation as hereinbefore described. This would allow positioning of a received bone screw at the fixed or pre-disposed angle. This may be particularly true for the cephelad-caudel screw pockets.

Figure 14:
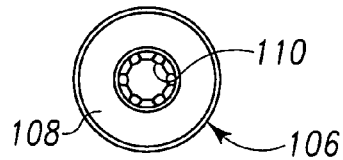
FIG. 14 is an end view of the fixed angle bone screw of FIG. 13 taken along line 14-14 thereof.
Figure 13:
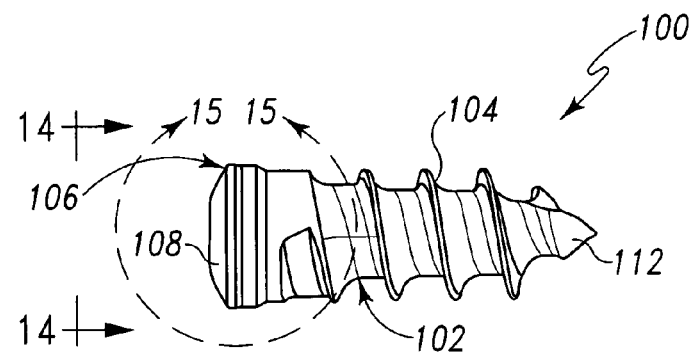
FIG. 13 is a side view of an exemplary fixed angle bone screw fashioned in accordance with the present principles.
Figure 15:
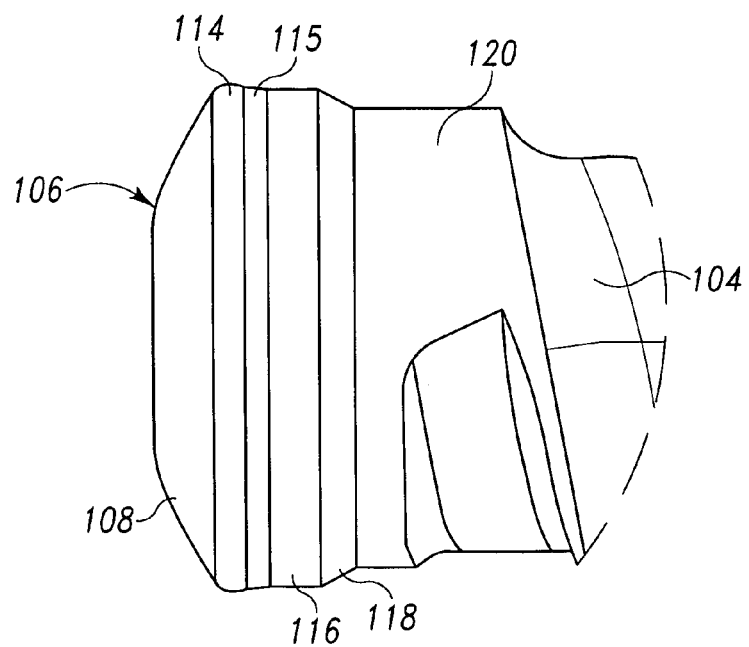
FIG. 15 is an enlarged portion of the fixed angle bone screw of FIG. 13 taken along circle 15-15 thereof.

Referring now to FIGS. 13-15, there is depicted an exemplary embodiment of a fixed angle bone screw, generally designated 100, that may be used with the present plate 10. The fixed angle bone screw 100 is characterized by a body 102 fashioned from a suitable biocompatible material such as titanium, stainless steel, alloys thereof, and the like. The body 102 has a shank 104 extending from a head 106. The shank 104 is in the form of an auger having a tip 112 and helical threads on the outer periphery thereof. The head 106 extends from the end of the shank 104 distal the tip 112. The head 106 includes an upper annular tapered area 108 that terminates in a socket 110. The socket 110 is provided on the longitudinal axis of the bone screw 100 and particularly the shank 104 and may be in the form of a hexalobe, or similar, drive or otherwise. The periphery of the head 106 is essentially annular.

Figure 27:
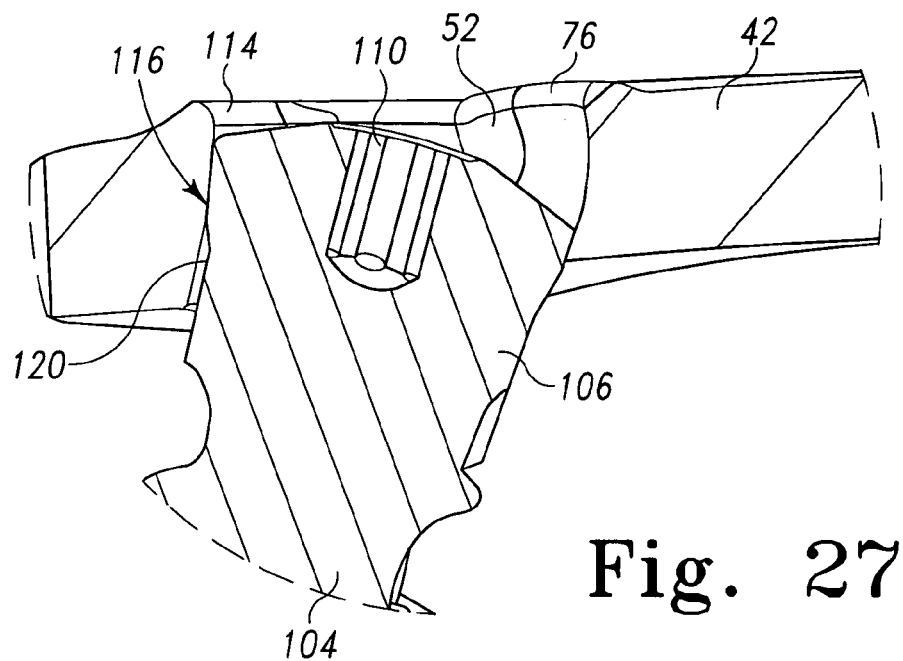
FIG. 27 is an enlarged portion of the sectional view of FIG. 22 taken along circle 27-27 thereof.

Referring to FIG. 15, the fixed angle screw head 106 includes a peripheral lip 114 that cooperates with a lip and undercut of a bone screw bore of the plate 10 as described herein in order to provide a snap feature between the bone screw bore configuration of the plate and the bone screw. Thus, as the bone screw 100 is received into a bone screw bore of the plate the peripheral lip 114 of the bone screw 100 axially passes the lip of the bone screw bore (see, e.g. FIG. 27) to snap into place in the undercut. Axial to the peripheral lip 114 is a transition area 115 that axially tapers from and helps define the peripheral lip 114 to an angulation area 116. The angulation area 116 of the fixed angle bone screw acts within the bone screw bore to prevent angulation once received therein. As particularly shown in FIG. 27, the larger diameter of the angulation area 116 prevents angulation of the bone screw in the bone screw bore (screw pocket) as the angulation area 116 meets the spherical walls of the screw pocket. Thus, once the boring angle of the fixed angle bone screw 100 is set, the angulation area 116 prevents further angulation through interaction with the geometry of the screw pocket. A second transition area 118 axially extends from the angulation area 116 to a shaft head 120. The fixed angle screw 100 may be used in any one of the bone screw bores of the plate 10.

Figure 17:
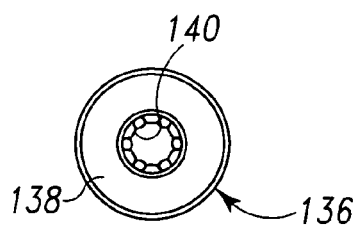
FIG. 17 is an end view of the variable angle bone screw of FIG. 16 taken along line 17-17 thereof.
Figure 16:
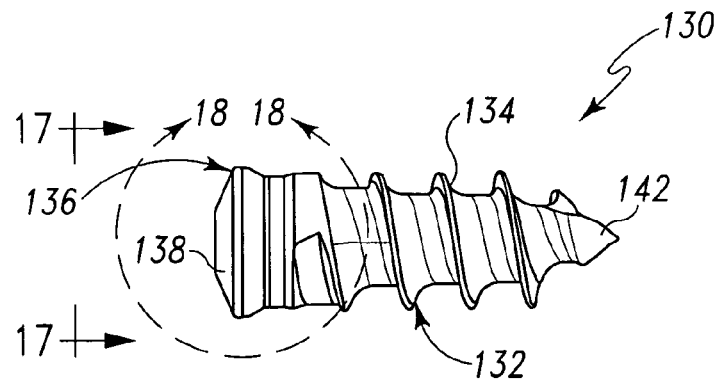
FIG. 16 is a side view of an exemplary variable angle bone screw fashioned in accordance with the present principles.
Figure 18:
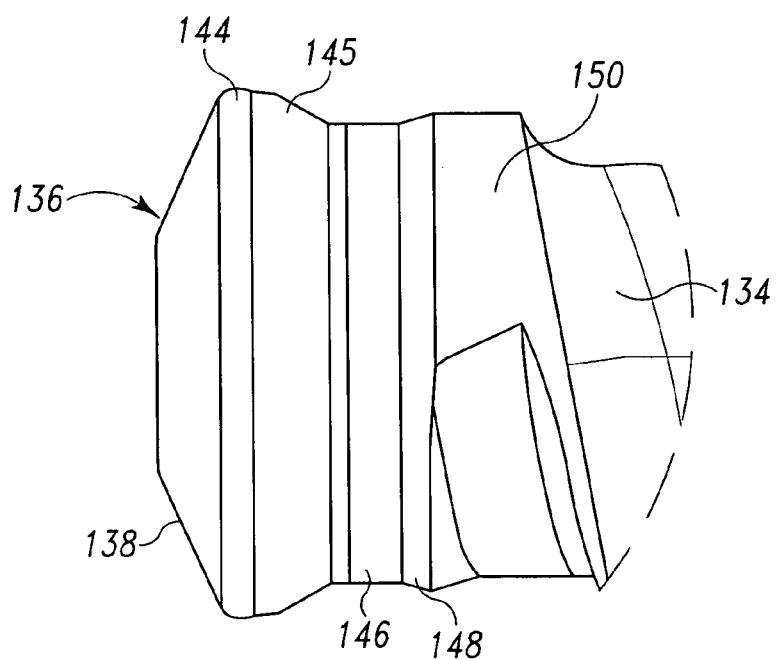
FIG. 18 is an enlarged portion of the variable angle bone screw of FIG. 16 taken along circle 18-18 thereof.

Referring now to FIGS. 16-18, there is depicted an exemplary embodiment of a variable angle bone screw, generally designated 130, that may be used with the present plate 10. The variable angle bone screw 130 is characterized by a body 132 fashioned from a suitable biocompatible material such as titanium, stainless steel, alloys thereof, and the like. The body 132 has a shank 134 extending from a head 136. The shank 134 is in the form of an auger having a tip 142 and helical threads on the outer periphery thereof. The head 136 extends from the end of the shank 134 distal the tip 142. The head 136 includes an upper annular tapered area 138 that terminates in a socket 140. The socket 140 is provided on the longitudinal axis of the bone screw 130 and particularly the shank 134 and may be in the form of a hexalobe drive or otherwise. The periphery of the head 136 is essentially annular.

Figure 28:
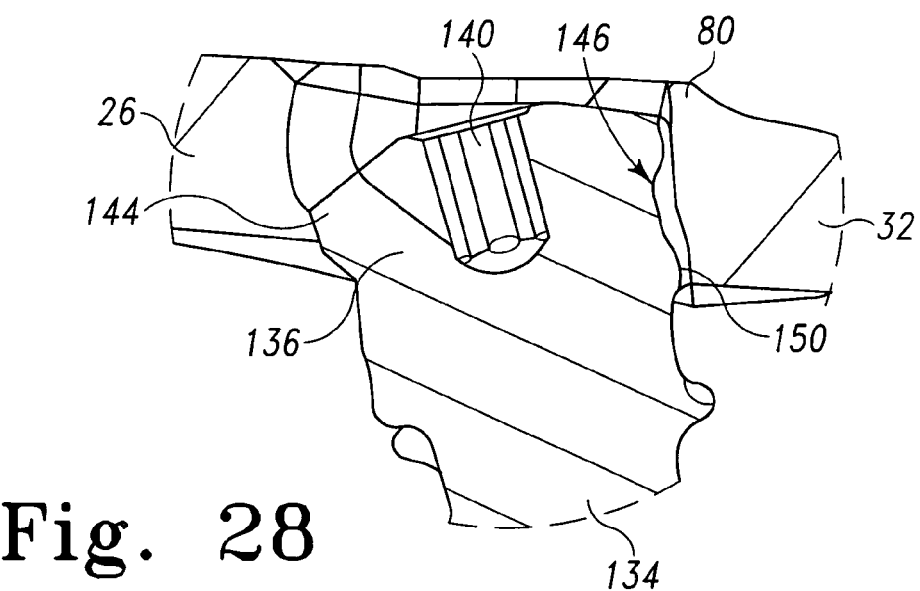
FIG. 28 is an enlarged portion of the sectional view of FIG. 22 taken along circle 28-28 thereof.

Referring to FIG. 18, the variable angle screw head 136 includes a peripheral lip 144 that cooperates with a lip and undercut of a bone screw bore of the plate 10 as described herein in order to provide a snap feature between the bone screw bore configuration of the plate and the bone screw. Thus, as the bone screw 130 is received into a bone screw bore of the plate the peripheral lip 144 of the bone screw 130 axially passes the lip of the bone screw bore (see, e.g. FIG. 28) to snap into place in the undercut. Axial to the peripheral lip 144 is a transition area 145 that axially tapers from and helps define the peripheral lip 144 to an angulation area 146. The angulation area 146 of the variable angle bone screw acts within the bone screw bore to allow angulation once received therein. As particularly shown in FIG. 28, the smaller or reduced diameter of the angulation area 146 allows angulation of the bone screw in the bone screw bore (screw pocket) as the angulation area 146 meets the spherical walls of the screw pocket. Thus, once the boring angle of the variable angle bone screw 130 is set, the angulation area 146 allows further angulation via the geometry of the screw pocket. A second transition area 148 axially extends from the angulation area 146 to a shaft head 150. The variable angle screw 130 may be used in any one of the bone screw bores of the plate 10. Such variable angle screws 130 are shown in the bone screw bores 60 and 62 of the middle section 14 (see, e.g. FIGS. 22, 25 and 26).

Figure 20:
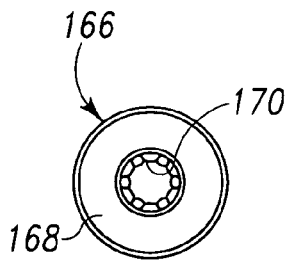
FIG. 20 is an end view of the emergency bone screw of FIG. 19 taken along line 20-20 thereof.
Figure 19:
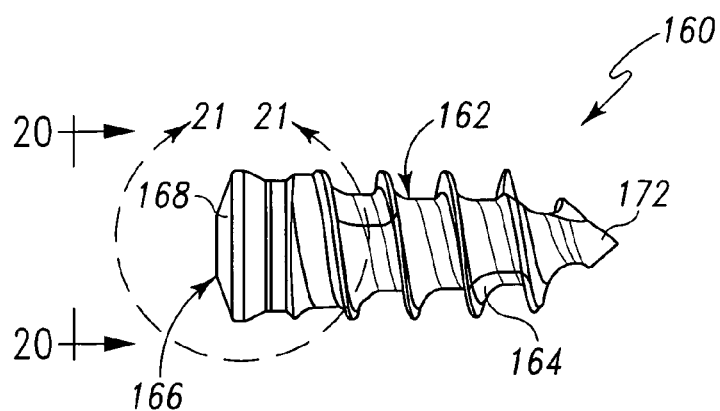
FIG. 19 is a side view of an emergency (variable) bone screw fashioned in accordance with the present principles.
Figure 21:
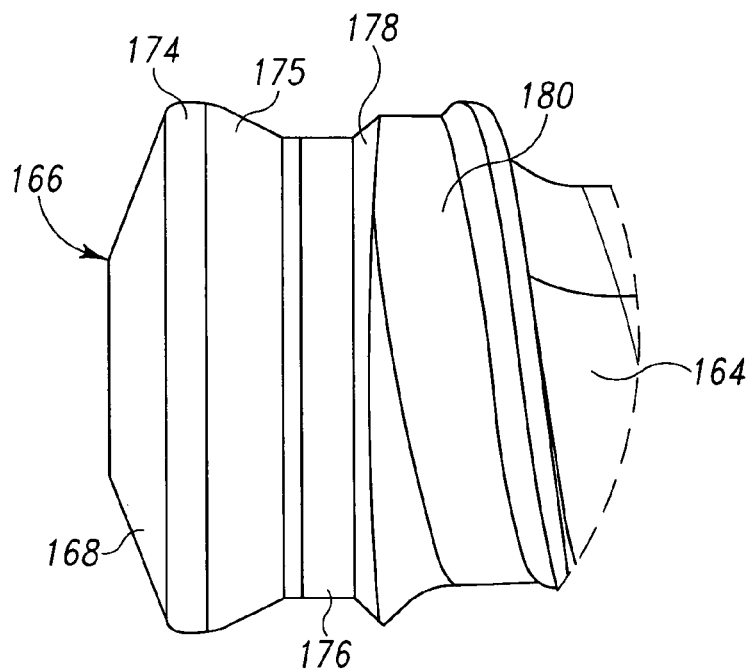
FIG. 21 is an enlarged portion of the emergency bone screw of FIG. 19 taken along circle 21-21 thereof.

Referring now to FIGS. 19-21, there is depicted an exemplary embodiment of an emergency (variable) bone screw, generally designated 160, that may be used with the present plate 10. The emergency bone screw 160 is characterized by a body 162 fashioned from a suitable biocompatible material such as titanium, stainless steel, alloys thereof, and the like. The body 162 has a shank 164 extending from a head 166. The shank 164 is in the form of an auger having a tip 172 and helical threads on the outer periphery thereof. The head 166 extends from the end of the shank 164 distal the tip 172. The head 166 includes an upper annular tapered area 168 that terminates in a socket 170. The socket 170 is provided on the longitudinal axis of the bone screw 160 and particularly the shank 164 and may be in the form of a hexalobe drive or otherwise. The periphery of the head 166 is essentially annular.

Referring to FIG. 21, the emergency screw head 166 includes a peripheral lip 174 that cooperates with a lip and undercut of a bone screw bore of the plate 10 as described herein in order to provide a snap feature between the bone screw bore configuration of the plate and the bone screw. Thus, as the bone screw 160 is received into a bone screw bore of the plate the peripheral lip 174 of the bone screw 160 axially passes the lip of the bone screw bore, such as previously described, to snap into place in the undercut. Axial to the peripheral lip 174 is an elongated transition area 175 that axially tapers from and helps define the peripheral lip 174 to an angulation area 176. The angulation area 176 of the emergency bone screw 160 acts within the bone screw bore to allow angulation once received therein. This is similar to that shown in FIG. 28 as described above with respect to variable angle bone screw 130. A second transition area 178 radially outwardly tapers from the angulation area 176 to an oversized shaft head 180. The emergency screw 160 may be used in any one of the bone screw bores of the plate 10. The helical threads of the emergency bone screw 160 are slightly larger in diameter than fixed or variable screws.

Figure 23:
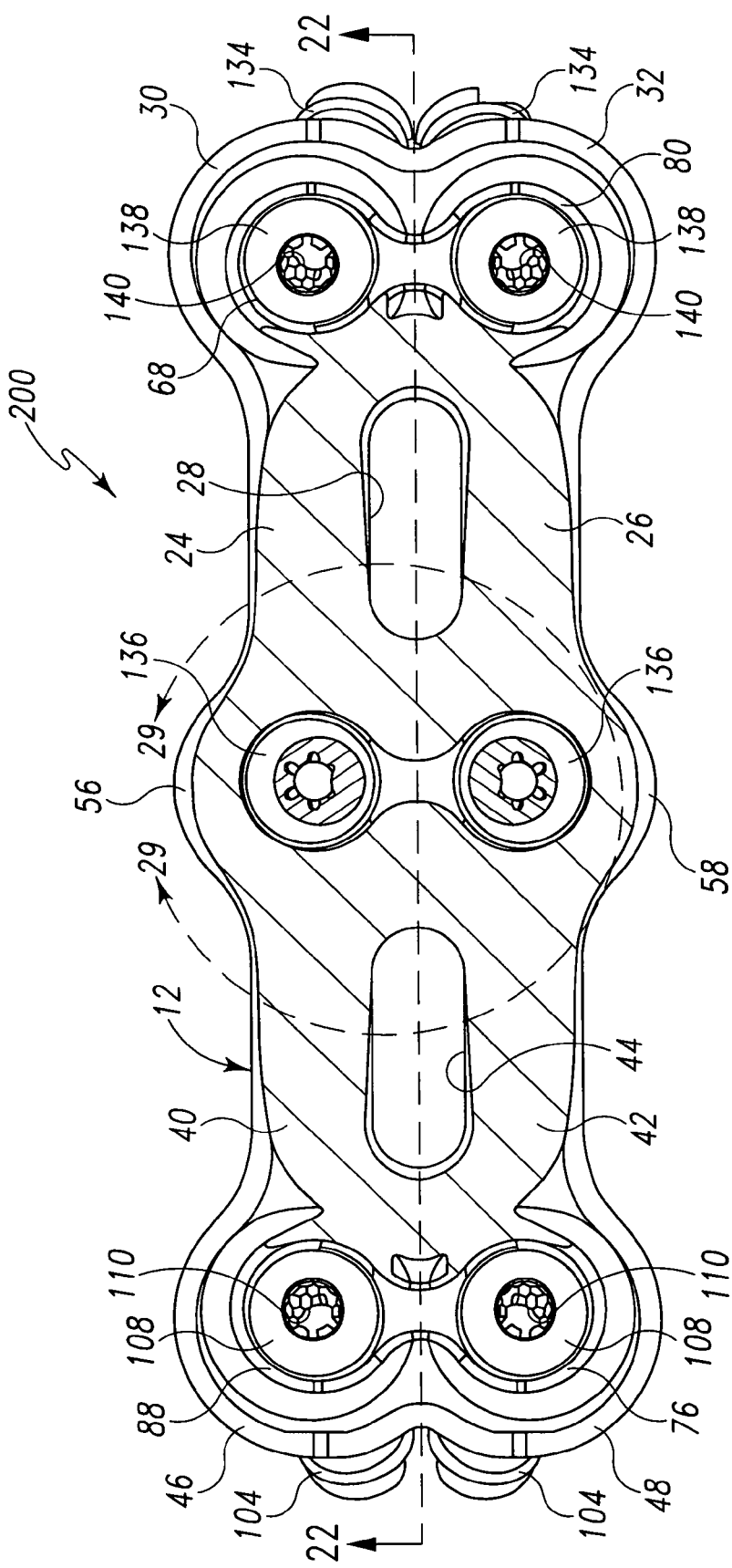
FIG. 23 is a sectional view of the present 2-L spine plate with various ones of the present bone screws of FIG. 22 taken along line 23-23 thereof.
Figure 29:
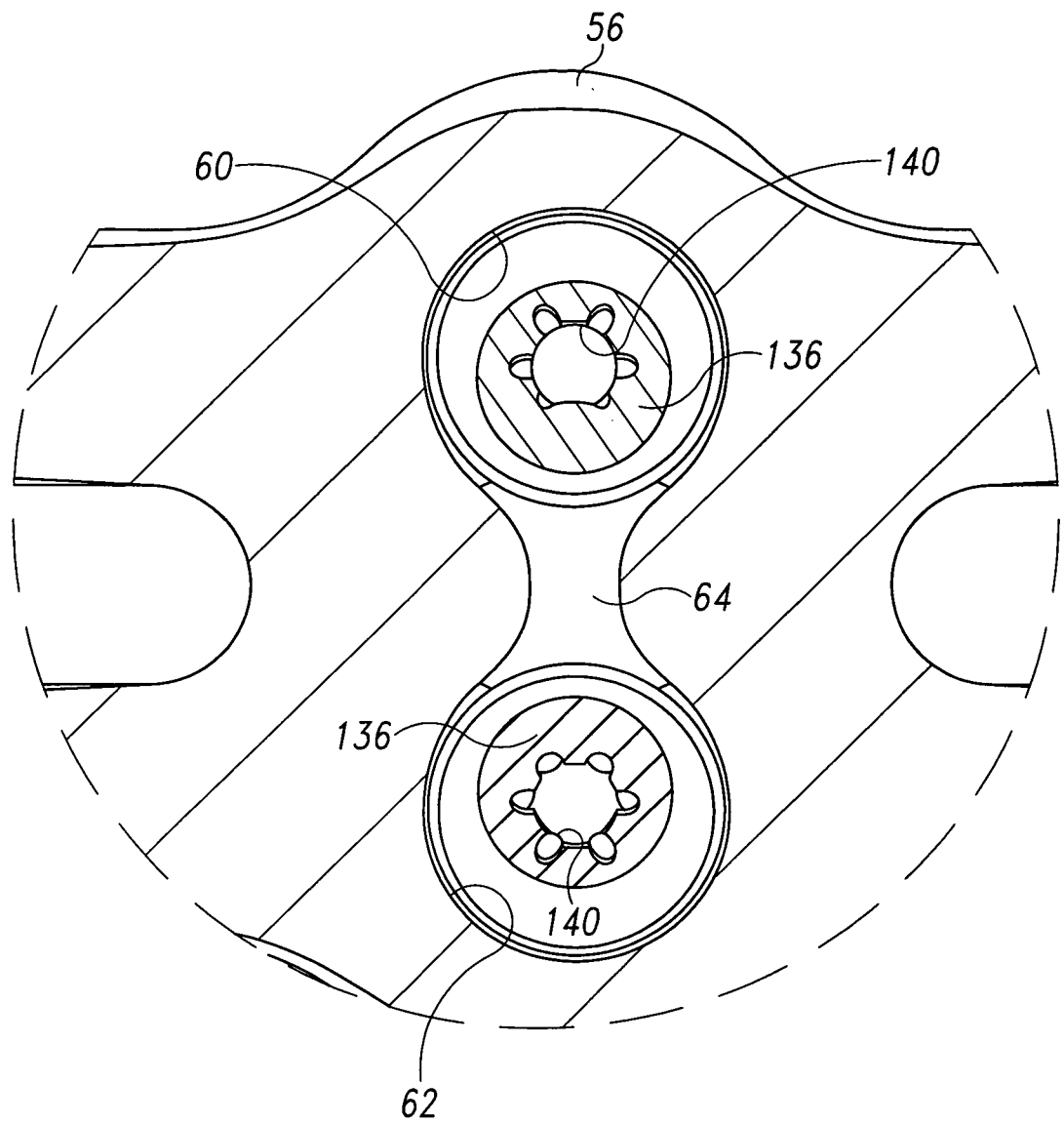
FIG. 29 is an enlarged portion of the sectional view of FIG. 23 taken along circle 29-29 thereof.

Reference is now made to FIGS. 23 and 29. When bone screws are installed in the bone screw bores of the middle section 14, the axis of the bone screws are at a centroid of the screw pocket.

It should be appreciated that a single level (1-L) spine plate has first and second ends each having first and second bone screw bores and a single neck section. A two level (2-L) spine plate has a middle section having first and second bone screw bores, first and second necks extending from each side of the middle section and each having an elongated window, a first end at the first neck distal the middle section and having first and second bone screw bores, and a second end at the second neck distal the middle section and having first and second bone screw bores. A three level (3-L) spine plate has two middle sections connected by a middle neck, then a neck and end section like the 2-L spine plate on an end of the two middle sections. This continues for higher level spine plates.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spine plate comprising:
   a body defining a posterior surface, an anterior surface, a first end, and a second end;
   a first pair of bone screw bores situated at the first end and separated from each other by a first distance, each one of the first pair of bone screw bores extending between the posterior surface of the body and the anterior surface of the body and having a first lip, the first lip defining a first boss that protrudes from the anterior surface of the body and extending around a majority of the respective bone screw bore;
   a second pair of bone screw bores situated at the second end and separated from each other by a second distance, each one of the second pair of bone screw bores extending between the posterior surface of the body and the anterior surface of the body and having a second lip, the second lip defining a second boss that protrudes from the anterior surface of the body and around a majority of the respective bone screw bore;
   a first channel in communication with the first pair of bone screw bores on the anterior surface and extending along the first distance;
   a second channel in communication with the second pair of bone screw bores on the anterior surface and extending along the second distance;
   wherein each first lip terminates at the first channel such that each first lip does not completely surround each respective bone screw bore in the first pair of bone screw bores; and
   wherein each second lip terminates at the second channel such that each second lip does not completely surround each respective bone screw bore in the second pair of bone screw bores.

2. The spine plate of claim 1, wherein:
the first channel comprises a width at its midpoint along the first distance that is less than a diameter of either the first pair of bone screw bores; and
the second channel comprises a width at its midpoint along the second distance that is less than a diameter of either the second pair of bone screw bores.

3. The spine plate of claim 2, wherein the first and second channels are configured as hour-glass shaped.

4. The spine plate of claim 1, further comprising:
a middle section defined in the body between the first end and the second end;
a third pair of bone screw bores situated at the middle section and separated from each other by a third distance, the third pair of bone screw bores extending between the posterior surface of the body and the anterior surface of the body; and
a third channel in communication with the third pair of bone screw bores and extending along the third distance.

5. The spine plate of claim 4, wherein each of the third pair of bone screw bores includes a third lip, the third lip defining a third boss that protrudes from the anterior surface of the body of the middle section and extends around a majority of the respective screw bone.

6. The spine plate of claim 5, wherein each third lip terminates at the third channel such that each third lip does not completely surround each respective bone screw bore in the third pair of bone screw bores.

7. The spine plate of claim 4, wherein the third channel is disposed in the anterior surface of the body.

8. The spine plate of claim 7, wherein the third channel narrows in width along the third distance.

9. The spine plate of claim 8, wherein:
the third channel narrows in width at a midpoint along the third distance.

10. The spine plate of claim 9, wherein the third channel is configured as hour-glass shaped.

11. A spine plate comprising:
a body defining a posterior surface, an anterior surface, a first end and a second end;
a first pair of bone screw bores at the first end of the body and separated from each other by a first distance, each one of the first pair of bone screw bores in communication with the posterior surface of the body and the anterior surface of the body and having a first lip, the first lip defining a first boss that protrudes from the anterior surface of the body and extending around a majority of the respective bone screw bore;
a second pair of bone screw bores at the second end of the body and separated from each other by a second distance, each one of the second pair of bone screw bores in communication with the posterior surface of the body and the anterior surface of the body and having a second lip, the second lip defining a second boss that protrudes from the anterior surface of the body and extending around a majority of the respective bone screw bore;
a first relief area on the anterior surface of the body and in communication with and extending between the first pair of bone screw bores along the first distance; and
a second relief area on the anterior surface of the body and in communication with extending between the second pair of bone screw bores along the second distance;
wherein each first lip extending around the first pair of bone screw bores and has a first end and a second end that are located proximate opposite edges of the first relief area, and wherein each second lip extending around the second pair of bone screw bores and has a first end and a second end that are located proximate opposite edges of the second relief area
wherein each first lip terminates at edges of the first relief area such that each first lip does not completely surround each respective bone screw bore in the first pair of bone screw bores; and
wherein each second lip terminates at edges of the second relief area such that each second lip does not completely surround each respective bone screw bore in the second pair of bone screw bores.

12. The spine plate of claim 11, wherein the first and second relief areas are each hour-glass shaped.

13. The spine plate of claim 11, further comprising:
a middle section defined in the body between the first end and the second end;
a third pair of bone screw bores at the middle section and separated from each other by a third distance, each one of the third pair of bone screw bores in communication with the posterior surface of the body and the anterior surface of the body; and
a third relief area in communication with and extending between the third pair of bone screw bores along the third distance.

14. The spine plate of claim 13, wherein each of the third pair of bone screw bores include a third lip, the third lip defining a third boss that protrudes from the anterior surface of the body of the middle section and extending around a majority of the respective screw bone.

15. The spine plate of claim 14, wherein each third lip terminates at the third relief area such that each third lip does not completely surround each respective bone screw bore in the third pair of bone screw bores.

16. The spine plate of claim 13, wherein the third relief area is disposed in the anterior surface of the body.

17. The spine plate of claim 16, wherein the third relief area narrows in width along the third distance.

18. The spine plate of claim 17, wherein:
the third relief area narrows in width at a midpoint along the third distance.

19. The spine plate of claim 18, wherein the third relief area is configured as hour-glass shaped.

20. A spine plate comprising:
a body defining a posterior surface, an anterior surface, a first end, and a second end;
a first pair of bone screw bores situated at the first end and separated from each other by a first distance, each one of the first pair of bone screw bores extending between the posterior surface of the body and the anterior surface of the body, and having a first lip, the first lip defining a first boss that protrudes from the anterior surface of the body and substantially around the respective bone screw bore;
a second pair of bone screw bores situated at the second end and separated from each other by a second distance, each one of the second pair of bone screw bores extending between the posterior surface of the body and the anterior surface of the body, and having a second lip, the second lip defining a second boss that protrudes from the anterior surface of the body and substantially around the respective bone screw bore;
wherein each first lip terminates at least partly around each respective bone screw bore in the first pair of bone screw bores such that each first lip does not completely surround each bone screw bore in the first pair of bone screw bores; and
wherein each second lip terminates at least partly around each respective bone screw bore in the second pair of bone screw bores such that each second lip does not completely surround each bone screw bore in the second pair of bone screw bores.

21. The spine plate of claim 20, further comprising:
a first channel extending along the first distance between the first pair of bone screw bores, the first channel comprising a width at its midpoint that is less than a diameter of either the first pair of bone screw bores; and
a second channel in communication with the second pair of bone screw bores and extending along the second distance, the second channel comprising a width at its midpoint along the second distance that is less than a diameter of either the second pair of bone screw bores.

22. The spine plate of claim 21, wherein each lip extending around first bone screw bore has a first end and a second end that are located proximate edges of the first channel, and where in each lip extending around second bone screw bore has a first end and a second end that are located proximate edges of the second channel.

23. The spine plate of claim 21, wherein the first channel, and the second channel are disposed in the anterior surface of the body.

24. The spine plate of claim 21, wherein each first lip terminates at the first channel and wherein each second lip terminates at the second channel.

* * * * *